(12) United States Patent  (10) Patent No.: US 8,858,525 B2
Bekele  (45) Date of Patent: Oct. 14, 2014

(54) NOISE DAMPENING FILM

(75) Inventor: Solomon Bekele, Taylors, SC (US)

(73) Assignee: Cryovac, Inc., Duncan, SC (US)

( * ) Notice: Subject to any disclaimer, the term of this patent is extended or adjusted under 35 U.S.C. 154(b) by 829 days.

(21) Appl. No.: 12/622,462

(22) Filed: Nov. 20, 2009

(65) Prior Publication Data

US 2011/0125114 A1  May 26, 2011

(51) Int. Cl.
*A61B 19/00* (2006.01)
*B32B 27/30* (2006.01)
*A61F 5/445* (2006.01)

(52) U.S. Cl.
CPC ............ *A61F 5/445* (2013.01); *B32B 27/302* (2013.01); *B32B 2307/102* (2013.01)
USPC ............................ 604/403; 604/332; 428/35.2

(58) Field of Classification Search
CPC ........... A61F 5/44; A61F 5/441; A61F 5/442; A61F 5/445; A61F 5/4404; A61F 5/4405; A61F 5/4407; B32B 27/302; B32B 2307/102
USPC .................................. 604/332, 403; 428/35.2
See application file for complete search history.

(56) References Cited

U.S. PATENT DOCUMENTS

| | | |
|---|---|---|
| 4,600,614 A | 7/1986 | Lancaster et al. |
| 4,640,865 A | 2/1987 | Lancaster et al. |
| 4,687,711 A | 8/1987 | Vietto et al. |
| 4,766,035 A | 8/1988 | Lancaster et al. |
| 4,906,495 A | 3/1990 | Martini et al. |
| 4,983,171 A | 1/1991 | Schirmer |
| 5,043,205 A | 8/1991 | Perazzo et al. |
| 5,110,390 A | 5/1992 | Martini et al. |
| 5,206,075 A | 4/1993 | Hodgson, Jr. |
| 5,237,018 A | 8/1993 | Sorathia et al. |
| 5,241,031 A | 8/1993 | Mehta |
| 5,272,236 A | 12/1993 | Lai |
| 5,278,272 A | 1/1994 | Lai |
| 5,290,842 A * | 3/1994 | Sasaki et al. .................. 524/271 |
| 5,399,396 A | 3/1995 | Ohlsson et al. |
| 5,407,713 A | 4/1995 | Wilfong et al. |
| 5,437,595 A | 8/1995 | Smith |

(Continued)

FOREIGN PATENT DOCUMENTS

EP  0 362 850 A2  4/1990
EP  1 149 598 A2  10/2001

(Continued)

OTHER PUBLICATIONS

Hwang et al. Thermal and Mechanical Properties of Amorphous Copolyester (PETG)/LCP blends. European Polymer Journal 35 (1999) 1439-1443.*

(Continued)

*Primary Examiner* — Philip R Wiest
*Assistant Examiner* — Ariana Zimbouski
(74) *Attorney, Agent, or Firm* — Alston & Bird LLP

(57) ABSTRACT

A noise dampening film is provided, and in particular, a film having at least one quiet layer that comprises a polymer resin and from about 5 to 50 weight percent of a styrene-vinyl polyisoprene-styrene block-co-polyisopyrene block triblock polymer. The quiet layer has a tan delta of at least about 0.27 or greater at a temperature range between about 17° C. and 40° C.

20 Claims, 2 Drawing Sheets

(56) References Cited

U.S. PATENT DOCUMENTS

Figure 1:
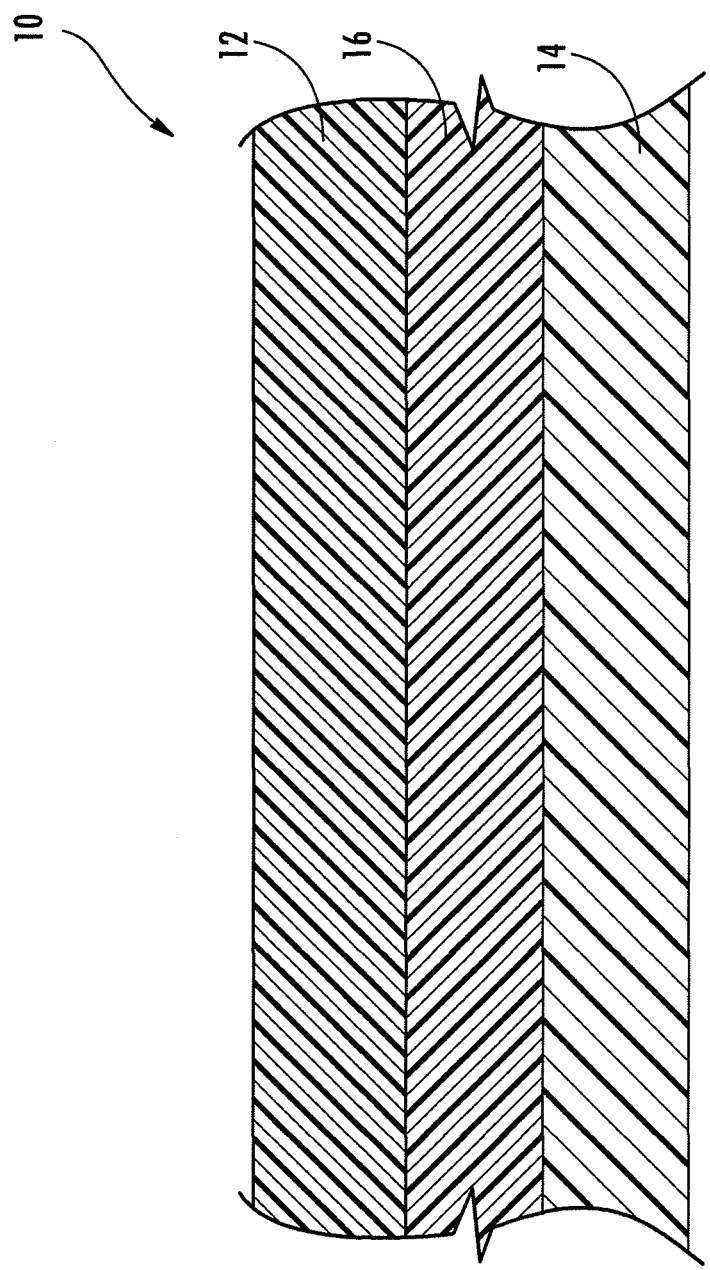

| | | |
|---|---|---|
| 5,455,091 A | 10/1995 | Oreglia et al. |
| 5,470,624 A | 11/1995 | Oreglia et al. |
| 5,496,295 A | 3/1996 | Wilfong et al. |
| 5,567,489 A | 10/1996 | Allen et al. |
| 5,658,625 A | 8/1997 | Bradfute et al. |
| 5,663,228 A * | 9/1997 | Sasaki et al. ............ 524/271 |
| 5,681,627 A * | 10/1997 | Mueller ............ 428/35.2 |
| 5,830,393 A * | 11/1998 | Nishikawa et al. ............ 264/50 |
| 5,846,620 A | 12/1998 | Compton |
| 5,895,694 A | 4/1999 | Zavadsky et al. |
| 6,143,383 A | 11/2000 | Giori |
| 6,244,441 B1 | 6/2001 | Ahlgren |
| 6,258,423 B1 | 7/2001 | Giori |
| 6,455,161 B1 * | 9/2002 | Regnier et al. ............ 428/412 |
| 6,558,809 B1 | 5/2003 | Kelch et al. |
| 6,572,959 B1 | 6/2003 | Buongiorno et al. |
| 6,620,474 B1 * | 9/2003 | Regnier et al. ............ 428/35.7 |
| 6,649,888 B2 | 11/2003 | Ryan et al. |
| 6,849,684 B2 | 2/2005 | Poppe et al. |
| 7,351,645 B2 * | 4/2008 | Ohashi et al. ............ 438/465 |
| 7,517,339 B2 | 4/2009 | Pedersen et al. |
| 2002/0025394 A1* | 2/2002 | Bradfute et al. ............ 428/34.9 |
| 2004/0087917 A1* | 5/2004 | Barakat et al. ............ 604/317 |
| 2004/0146671 A1 | 7/2004 | Szabo et al. |
| 2007/0142557 A1* | 6/2007 | Karsten et al. ............ 525/240 |
| 2009/0159362 A1 | 6/2009 | Boure et al. |

FOREIGN PATENT DOCUMENTS

| | | |
|---|---|---|
| EP | 1149598 | * 10/2001 |
| JP | 4 357957 | 12/1992 |
| JP | 2000-33674 | 2/2000 |
| WO | WO-90/03414 | 4/1990 |
| WO | WO-93/03093 | 2/1993 |
| WO | WO 00/69629 | 11/2000 |
| WO | WO 2011/017477 A1 | 2/2011 |

OTHER PUBLICATIONS

MSDS of Hybrar 5127.*

Kuraray website with HYBRAR description (http://www.kuraray.us.com/products/elastomers/hybrar/).*

Hwang et al. (Thermal and mechanical properties of amorphous copolyester (PETG)/LCP blends, European Polymer Journal, vol. 35, pp. 1439-1443 (1999)).*

International Search Report and Written Opinion for International Application No. PCT/US2010/056289 mailed Feb. 17, 2011.

International Search Report and Written Opinion for International Application No. PCT/US2010/056285 mailed Feb. 16, 2011.

* cited by examiner

NOISE DAMPENING FILM

FIELD OF THE INVENTION

The present invention relates generally to films for the production of pouches and in particular noise dampening films that can be used in the production of medical packaging.

BACKGROUND OF THE INVENTION

Multilayer films having gas and odor barrier properties are well known and widely used in food and medical packaging applications. Generally, it is desirable for such films to have good impact resistance, flexibility, barrier properties, and desirable optical properties.

Where the films are to be used in medical applications, such as ostomy applications, they must also possess a unique combination of odor and moisture barrier properties as well as low noise, softness, heat or radio-frequency sealability, skin compatibility, and comfort. Such films have been provided in the past through the use of multi-ply film laminates where at least one of the plies is oxygen and moisture vapor impermeable.

In addition to barrier properties, it is often desirable that polymeric films for use in ostomy applications to not emit noise during use, such as when the film is crumpled or bent, so that the presence of the ostomy pouch is concealed from others. In particular, it has been found that the use of ostomy pouches makes the patient feel uneasy about such containers emitting, especially as the patient moves around, noise of a low but still audible intensity level. Most polymeric films, especially multilayer polymer films comprised of individual polymeric film layers having different rigidities (i.e., modulus), emit noise when crumpled. Such noise may alert others to the presence of the ostomy pouch, which can result in embarrassment to the wearer.

Accordingly, there still exists a need for polymeric films having sound dampening properties.

BRIEF SUMMARY OF THE INVENTION

The present invention is directed to a noise dampening film, and in particular to a film having at least one quiet layer that comprises a polymer resin and from about 5 to 50 weight percent of a styrene-vinyl polyisoprene-styrene block-co-polyisopyrene block triblock polymer. The quiet layer has a tan delta of at least about 0.27 or greater at a temperature range between about 17° C. and 40° C. In particular, films in accordance with the present invention have improved noise dampening properties at temperature ranges that are within the body temperature range of the person using the pouch. As a result, films in accordance with the present invention provide improved reductions in emitted noise levels at normal body temperatures and are particularly suited in medical applications, such as in ostomy pouches.

In a further aspect, the present invention also provides a noise dampening film that is also RF sealable. In one embodiment, the present invention provides a film having at least one exterior layers that comprises a blend of an ethylene/alpha-olefin copolymer and an ethylene acrylate copolymer, and at least one interior quiet layer comprising a blend of an ethylene/alpha-olefin copolymer, an ethylene acrylate copolymer, and from 10 to 50 weight % of a styrene-vinyl polyisoprene-styrene block-co-polyisopyrene block triblock polymer. In one particular embodiment, the film may include two such quiet interior layers.

Suitable ethylene acrylate copolymers for use in the invention include of ethylene vinyl acetate (EVA), ethylene butyl acrylate (EBA), and ethylene methyl acrylate (EMA), ethylene-co-n-butyl acrylate-co-carbon monoxide, ethylene-co-n-vinyl acetate-co-carbon monoxide, ethylene-co-n-butyl acrylate-co-glycidyl methacrylate, and combinations thereof. In one embodiment, a RF sealable film is provided in which the film includes at least one layer comprising a blend of an ethylene/alpha-olefin copolymer and an ethylene acrylate copolymer selected from the group consisting of ethylene vinyl acetate (EVA), ethylene butyl acrylate (EBA), and ethylene methyl acrylate (EMA), and combinations thereof. By blending an ethylene/alpha olefin with an ethylene acrylate copolymer, wherein the amount of the ethylene acrylate copolymer is from about 20 to 80 weight percent of the blend, RF sealable films with peel strengths in excess of 500 g/inch can be obtained. The amount of ethylene acrylate copolymer in the exterior layer is typically from about 20 to 80 weight %, based on the total weight of the film, and more typically from about 25 to 70 weight %. In one embodiment, the amount of ethylene acrylate copolymer in the exterior layer is at least about 50 weight %.

In a preferred embodiment, the ethylene acrylate copolymer comprises ethylene vinyl acetate wherein the vinyl acetate content in the EVA component is from about 12 to 28%, with a content of about 28% being somewhat more preferred. A preferred ethylene/alpha-olefin copolymer for use in the present invention is linear low density polyethylene based on 1-butene.

In one embodiment, a three-layer film is provided comprising a first exterior layer, a second exterior layer, and an interior layer positioned between the first and second exterior layers. The exterior layers each comprise a blend of an ethylene/alpha-olefin copolymer, an ethylene acrylate copolymer, and a styrene-vinyl polyisoprene-styrene block-co-polyisopyrene block triblock polymer. The interior layer may comprise a barrier material such as PVDC.

In a further aspect of the present invention, a seven-layer RF sealable film is provided. In this embodiment, the film includes two exterior layers comprising a blend of an ethylene/alpha-olefin copolymer and an ethylene acrylate copolymer, a core barrier layer, first and second interior layers disposed between the core and the outer exterior layers. The first and second interiors layers also comprise a blend of an ethylene/alpha-olefin copolymer and an ethylene acrylate copolymer, and further include a styrene-vinyl polyisoprene-styrene block-co-polyisopyrene block triblock polymer. A tie/adhesive layer is disposed between each of the first and second interior layers and the core layer. In one embodiment, the first and second interior layers define bulk layers of the film and generally each have a thickness that is about 20 to 40% of the total thickness of the film. In comparison, the first and second exterior layers have a thickness that typically ranges from about 25 to 75% of the thickness of the first and second interior layers.

The amount of the ethylene acrylate copolymer in the exterior layers generally ranges from about 50 to 80 weight percent whereas the content of the ethylene acrylate copolymer in the first and second interior layers is typically from about 40 to 60 weight percent.

Films in accordance with the present invention provide improved noise dampening, good RF sealability and are particularly useful in medical pouch applications, such as ostomy bags and the like.

BRIEF DESCRIPTION OF THE SEVERAL VIEWS OF THE DRAWING(S)

Figure 2:
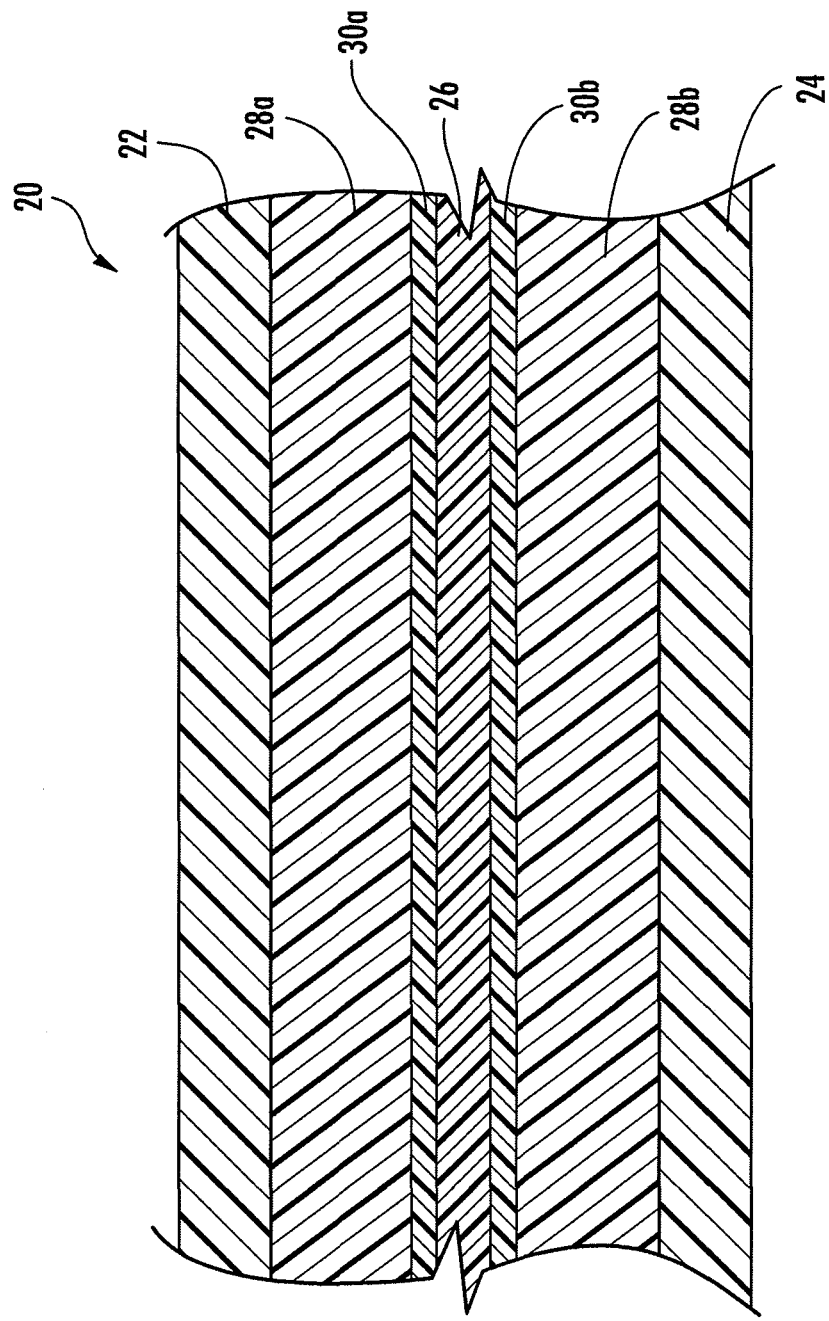

Having thus described the invention in general terms, reference will now be made to the accompanying drawings, which are not necessarily drawn to scale, and wherein:

FIG. 1 is a schematic cross-section of a three-layer film in accordance with the present invention; and FIG. 2 is a schematic cross-section of a seven-layer film in accordance with the present invention.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the invention are directed to a composition and films having noise dampening properties. In particular, the invention provides a film having at least one layer having noise dampening properties. This noise dampening layer, also referred to as a quiet layer, has a Tangent Delta value of at least about 0.27 at a temperature range between about 17° C. and 40° C. Films in accordance with the present invention can be used to form a variety of packaging structures including pouches, bags, satchels and the like. In one embodiment, the present invention is directed to pouches for medical applications, including the packaging of medical solutions, containment of human drainage, such as ostomy, colostomy, urostomy pouches, and the like.

As discussed previously, the present invention provides a multilayer film having at least one quiet layer having a tangent delta value of at least about 0.27 or greater at a temperature range between about 17° C. and 40° C. The tangent delta value (also referred to as the tan delta) refers to a material's ability to dampen noise and vibration, and is related to the material's complex Young's modulus $$E^* = E' + iE'',$$

where E' is the real, elastic, or in-phase modulus, and E'' is the imaginary, viscous, loss, or out-of-phase modulus; $i = \sqrt{-1}$. A measure of the mechanical energy dissipation as heat in a viscoelastic material is the ratio E''/E', which is also referred to as the damping factor, tangent delta.

In the present invention, the quiet layer comprises a blend of a polymer resin and an effective amount of a styrene-vinyl polyisoprene-styrene block-co-polyisopyrene block triblock polymer so that the layer has a tan delta of at least about 0.27 or greater at a temperature range between about 17° C. and 40° C. Unless stated to the contrary, tan delta measurements were determined in accordance with ASTM D 4065. It has been found that films having at least one quiet layer in which the quiet layer has a tan delta of at least about 0.27 or greater at a temperature range between about 17° C. and 40° C. have improved low noise performance in medical applications. During normal use of ostomy pouches, the temperature to which the pouch is exposed is typically greater than that of the ambient room temperature. This increase is typically a result of the temperature of the fluids within the pouch or the proximity of the pouch to the wearer. Films in accordance with the present invention provide improved reductions in emitted noise levels at a slightly elevated temperature range and are particularly suited in medical applications, such as in ostomy pouches.

In one embodiment as shown in FIG. 1, a three-layer film 10 is provide in which the film 10 includes a first exterior layer 12, a second exterior layer 14, and an interior layer 16 positioned between exterior layers 12 and 14. It should be noted, however, that additional layers, e.g., adhesive layers or additional function layers, such as barrier layers, may be included in film 10 as desired.

In the embodiment illustrated in FIG. 1, at least one of the layers comprises a quiet layer. For instance, at least one of exterior layers 12, 14 or interior layer 16 of the film comprises a blend of a polymer resin and a styrene-vinyl polyisoprene-styrene block-co-polyisopyrene block triblock polymer ("SVPSPI"). Generally, the amount of SVSPI polymer in the quiet layer ranges from about 5 to 50 weight percent, and in particular, from about 10 to 50 weight percent, with an amount of 10 to 40 being somewhat more typical.

The polymer resin in the quiet layer can be selected from a wide variety of materials depending on the particular function of the layer in which the SVSPI polymer is incorporated. For example, the SVSPI polymer can be incorporated into any one of exterior or interior layers, which may include a sealant layer, adhesive/tie layer, bulk layer, barrier layer, etc. Examples of polymeric materials that can be blended with the SVSPI polymer include ethylene acrylates, such as ethylene vinyl acetate, ethylene methyl acrylate, ethylene butyl acrylate, and ethylene/alpha-olefin copolymers having densities from about 0.84 to 0.93.

In one embodiment, the film 10 of FIG. 1 is directed to an RF sealable film that is particularly useful in the construction of ostomy pouches. In this embodiment, film 10 includes at least one exterior layer comprising an ethylene acrylate copolymer. In an exemplary embodiment, the first and second exterior layers 12, 14 of the film are both quiet layers and comprise a blend of an ethylene acrylate copolymer and a SVSPI polymer. Interior layer 16 of the film may comprise a barrier material as discussed more fully below.

Suitable ethylene acrylate copolymers for use in ostomy pouch applications of the present invention may include of ethylene vinyl acetate (EVA), ethylene butyl acrylate (EBA), and ethylene methyl acrylate (EMA). Other suitable may include ethylene-co-n-butyl acrylate-co-carbon monoxide available from DuPont under the tradename Elvaloy HP771™, ethylene-co-n-vinyl acetate-co-carbon monoxide available from DuPont under the tradename Elvaloy HP4924™, and ethylene-co-n-butyl acrylate-co-glycidyl methacrylate available from DuPont under the tradename Elvaloy PTW™. In one embodiment, a noise dampening, RF sealable film is provided in which the film includes a layer comprising a blend of an SVPSI polymer, ethylene/alpha-olefin copolymer and an ethylene acrylate copolymer selected from the group consisting of ethylene vinyl acetate (EVA), ethylene butyl acrylate (EBA), and ethylene methyl acrylate (EMA), and combinations thereof. The inventors of the present invention have discovered that by blending an ethylene/alpha olefin with an ethylene acrylate copolymer, wherein the amount of the ethylene acrylate copolymer is from about 20 to 80 weight percent of the blend, RF sealable films with peel strengths in excess of 500 g/inch can be obtained. The amount of ethylene acrylate copolymer in the exterior layer is typically from about 50 to 70 weight %, based on the total weight of the film, and more typically at least about 50 weight %.

In a preferred embodiment, the ethylene acrylate copolymer comprises ethylene vinyl acetate. The term "EVA" or "ethylene vinyl acetate copolymer" refers generally to a copolymer formed with ethylene and vinyl acetate monomers in which the ethylene derived units in the copolymer are present in major amounts, preferably from about 60 to 98% by weight, and the vinyl acetate-derived units in the copolymer are present in minor amounts, preferably from about 2 to 40 percent by weight of the total. In this embodiment, the EVA may have a high vinyl acetate content, for example, from about 12 to 28%, with a content of about 28% being somewhat more preferred.

In a further embodiment of the invention, the exterior layers comprise a blend of a blend of an ethylene acrylate copolymer, such as those discussed above, an ethylene/alpha-olefin copolymer, and a SVSPI polymer. In this embodiment, the content of the ethylene acrylate copolymer typically ranges from 20 to 80 weight percent of each layer. In embodiments comprising EVA, the amount of ethylene acrylate copolymer in the quiet layer is typically at least 50 weight percent. In embodiments comprising EMA or EBA, the amount of ethylene acrylate copolymer is generally at least about 35 weight percent. Suitable ethylene/alpha-olefin copolymers for use in the present invention are discussed in greater detail below.

In RF sealable film applications, the film has a dielectric loss factor of at least 0.02 and is capable of being radio frequency sealed. Unless stated to the contrary, the dielectric loss factor was determined in accordance with ASTM D 150. Films in accordance with the invention provide RF seals having peel strengths on the order of 500 g/in or greater as measure in accordance with ASTM F 88. In some embodiments, the peel strength of the RF seals are greater than 1000 g/in., and in particular, greater than about 2,000 g/in.

When the multilayer film of the present invention is used to form a pouch, such as an I.V. bag, ostomy pouch, or air-bladder portion of a compression device, the first exterior layer preferably forms the outer surface of the pouch (i.e., the surface which is exposed to the environment) while the second exterior layer forms the inner surface of the pouch (i.e., the surface which is in contact with the inside of the pouch and, therefore, with the product, drainage, or air which is enclosed within the pouch). In this fashion, the first exterior layer provides the pouch with abuse-resistance, and gloss, as well as a high degree of flexibility and strength as noted above. The second exterior layer serves as a sealant layer. In this role, peripheral portions of the second exterior layer are joined, e.g., by radio frequency (RF) sealing, to form an enclosure. In addition to RF sealing, embodiments of the invention can also be sealed with heat sealing, ultrasound sealing, and the like.

Interior layer 16 is typically serves as a functional or core layer of the film. In one embodiment, interior layer 16 is comprised of a material having barrier properties so that the film is substantially impervious to vapor and liquids. As noted above, embodiments of the multilayer film of the present invention include an interior layer positioned between the first and second exterior layers. Depending upon the particular application for which the multilayer film is to be used, the interior layer may provide additional desired properties, e.g., oxygen-barrier functionality, strength, RF sealability, or melt strength. In addition, the interior layer can serve to reduce the cost of the film by allowing less material to be used in the other layers of the film structure.

Suitable materials from which the interior layer may be selected include poly(ethylene/vinyl alcohol) (EVOH), poly (vinyl alcohol) (PVOH), polyacrylonitrile (PAN), polyesters such as polyethylene terephthalate (PET), and polyethylene naphthalate (PEN), and their copolyesters, polyvinyl chloride (PVC and its copolymers), polyvinylidene chloride (PVDC and its copolymers), and polyamides such as polycaprolactam (nylon 6), metaxylylene adipamide (MXD6), MXD6/MXDI and copolyamides based on m-xylylenediamine, hexamethylene adipamide (nylon 66), amorphous polyamides such as nylon 6I, 6T, as well as various amide copolymers and various blends of the above. Additional oxygen barriers include metal foil layers, metal coatings, depositions of metal, metal oxides such as silica ($SiO_x$), alumina, nano clays and vermiculite can also provide oxygen barrier properties.

Although ethylene/vinyl alcohol copolymer is not as flexible as the other listed materials, it may nevertheless be useful in certain applications. Polyvinylidene chloride (PVDC) homopolymers and, more preferably, copolymers, are preferred for use in the interior layer when gas-barrier functionality is desired in the multilayer film of the present invention. This would be the case when the film is formed into, e.g., an ostomy-type drainage pouch to prevent odors from escaping the pouch. One suitable polymer that may be used in accordance with the present invention comprises PVDC and methyl acrylate copolymer available from Solvin under the tradename Ixan PV910. Other suitable PVDC polymers that may be used in accordance with the present invention are available from Dow Chemical under the tradename SARAN.

FIG. 2 illustrates another embodiment of the invention in which a seven-layer film 20 is provided that is also particularly useful in ostomy pouch applications in which one of the layers of the film is a quiet layer. In one particular embodiment, the present invention provides an RF sealable film in which exterior layers 22, 24 comprise a blend of an ethylene/alpha-olefin copolymer and an ethylene acrylate copolymer. Interior layer 26 may be a functional or core layer as discussed above. Interior layers 28a and 28b are disposed between the outer exterior layers 22, 24 and interior layer 26. Adhesive or tie layers 30a, 30b are each disposed between interior layers 28a, 28b and interior layer 26. In a preferred embodiment, the corresponding layers disposed on opposite sides of interior layer 26 are the same or similar to each other. For example, layers 22 and 24 are preferably the same or of a similar composition as are each other as are layers 28a and 28b. Interior layer 26 may comprise a barrier material such as PVDC. Suitable materials for the adhesive/tie layer 30a, 30b are discussed above.

In the illustrated embodiment, the interior layers 28a and 28b are the bulk layers of the film and help to provide strength and integrity to the film. In one embodiment, interior layers 28a and 28b also contribute to the RF sealability of the film. In one such embodiment, interior layers 28a and 28b and each exterior layer comprise a blend of an ethylene/alpha-olefin copolymer and an ethylene acrylate copolymer. The SVSPI polymer may be located in any one or more of the interior or exterior layers. In one particular embodiment, the exterior layers may comprise from about 40 to 80 weight percent of an ethylene acrylate copolymer, and from about 20 to 50 weight percent of an ethylene/alpha-olefin, and the interior layers 28a and 28b may each independently comprise a blend of SVSPI, LLDPE and EVA in which the EVA is present in an amount from about 30 to 60 weight percent and the LLDPE is present in an amount from about 20 to 40 weight percent, and the SVSPI is present in an amount from 10 to 50 weight percent. In this embodiment, interior layers 28a and 28b are both quiet layers of the film. The interior layers 28a and 28b may also each comprise a blend LLDPE, EVA in which the EVA is present in an amount of at least 50 weight percent and the LLDPE is present in an amount from about 35 to 50 weight percent.

A wide variety of ethylene/alpha-olefin (EAO) copolymers may be used in the practice of the present invention. The term "ethylene/alpha-olefin copolymer" generally designates copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches. These polymers are obtained by low pressure polymerization processes and the side branching which is present will be short compared to non-linear polyethylenes (e.g., LDPE, a polyethylene homopolymer). The polyethylene polymers may be either heterogeneous or homogeneous.

Heterogeneous ethylene/alpha-olefin copolymers are ethylene/alpha-olefin copolymerization reaction products of relatively wide variation in molecular weight and composition distribution, and which are prepared using conventional Ziegler-Natta or other heterogeneous catalysts. Examples of heterogeneous ethylene/alpha-olefins include linear low density polyethylene (LLDPE), linear medium density polyethylene (LMDPE), very low density polyethylene (VLDPE), and ultra-low density polyethylene (ULDPE). LLDPE is generally understood to include that group of heterogeneous ethylene/alpha-olefin copolymers which fall into the density range of about 0.915 to about 0.94 g/cc. Sometimes linear polyethylene in the density range from about 0.926 to about 0.94 is referred to as LMDPE. Lower density heterogeneous ethylene/alpha-olefin copolymers are VLDPE (typically used to refer to the ethylene/butene copolymers available from Union Carbide with a density ranging from about 0.88 to about 0.91 g/cc) and ULDPE (typically used to refer to the ethylene/octene copolymers supplied by Dow). EAOs are copolymers of ethylene and one or more alpha-olefins, the copolymer having ethylene as the majority mole-percentage content. In some embodiments, the comonomer includes one or more $C_3$-$C_{20}$ alpha-olefins, such as one or more $C_4$-$C_{12}$ alpha-olefins, or one or more $C_4$-$C_8$ alpha-olefins. Particularly useful alpha-olefins include 1-butene, 1-hexene, 1-octene, and mixtures thereof.

Useful EAOs include those having a density of less than about any of the following: 0.925, 0.922, 0.92, 0.917, 0.915, 0.912, 0.91, 0.907, 0.905, 0.903, 0.9, and 0.86 grams/cubic centimeter (g/cm³). Unless otherwise indicated, all densities herein are measured according to ASTM D1505. In one embodiment, the EAO has a density from about 0.84 to 0.91 g/cm³.

As is known in the art, heterogeneous polymers have a relatively wide variation in molecular weight and composition distribution. Heterogeneous polymers may be prepared with, for example, conventional Ziegler Natta catalysts.

On the other hand, homogeneous polymers are typically prepared using metallocene or other single site-type catalysts. Such single-site catalysts typically have only one type of catalytic site, which is believed to be the basis for the homogeneity of the polymers resulting from the polymerization. Homogeneous polymers are structurally different from heterogeneous polymers in that homogeneous polymers exhibit a relatively even sequencing of comonomers within a chain, a mirroring of sequence distribution in all chains, and a similarity of length of all chains. As a result, homogeneous polymers have relatively narrow molecular weight and composition distributions. Examples of homogeneous polymers include the metallocene-catalyzed linear homogeneous ethylene/alpha-olefin copolymer resins available from the Exxon Chemical Company (Baytown, Tex.) under the EXACT trademark, linear homogeneous ethylene/alpha-olefin copolymer resins available from the Mitsui Petrochemical Corporation under the TAFMER trademark, and long-chain branched, metallocene-catalyzed homogeneous ethylene/alpha-olefin copolymer resins available from the Dow Chemical Company under the AFFINITY trademark.

More particularly, homogeneous ethylene/alpha-olefin copolymers may be characterized by one or more properties known to those of skill in the art, such as molecular weight distribution ($M_w/M_n$), composition distribution breadth index (CDBI), narrow melting point range, and single melt point behavior. The molecular weight distribution ($M_w/M_n$), also known as "polydispersity," may be determined by gel permeation chromatography. Homogeneous ethylene/alpha-olefin copolymers which can be used in the present invention generally have an $M_w/M_n$ of less than 2.7; such as from about 1.9 to 2.5; or from about 1.9 to 2.3 (in contrast heterogeneous ethylene/alpha-olefin copolymers generally have a $M_w/M_n$ of at least 3). The composition distribution breadth index (CDBI) of such homogeneous ethylene/alpha-olefin copolymers will generally be greater than about 70 percent. The CDBI is defined as the weight percent of the copolymer molecules having a comonomer content within 50 percent (i.e., plus or minus 50%) of the median total molar comonomer content. The CDBI of linear ethylene homopolymer is defined to be 100%. The Composition Distribution Breadth Index (CDBI) is determined via the technique of Temperature Rising Elution Fractionation (TREF). CDBI determination may be used to distinguish homogeneous copolymers (i.e., narrow composition distribution as assessed by CDBI values generally above 70%) from VLDPEs available commercially which generally have a broad composition distribution as assessed by CDBI values generally less than 55%. TREF data and calculations therefrom for determination of CDBI of a copolymer may be calculated from data obtained from techniques known in the art, such as, for example, temperature rising elution fractionation as described, for example, in Wild et. al., J. Poly. Sci. Poly. Phys. Ed., Vol. 20, p. 441 (1982). In some embodiments, homogeneous ethylene/alpha-olefin copolymers have a CDBI greater than about 70%, i.e., a CDBI of from about 70% to 99%. In general, homogeneous ethylene/alpha-olefin copolymers useful in the present invention also exhibit a relatively narrow melting point range, in comparison with "heterogeneous copolymers", i.e., polymers having a CDBI of less than 55%. In some embodiments, the homogeneous ethylene/alpha-olefin copolymers exhibit an essentially singular melting point characteristic, with a peak melting point ($T_m$), as determined by Differential Scanning calorimetry (DSC), of from about 60° C. to 105° C. In one embodiment, the homogeneous copolymer has a DSC peak $T_m$ of from about 80° C. to 100° C. As used herein, the phrase "essentially single melting point" means that at least about 80%, by weight, of the material corresponds to a single $T_m$ peak at a temperature within the range of from about 60° C. to 105° C., and essentially no substantial fraction of the material has a peak melting point in excess of about 115° C., as determined by DSC analysis. DSC measurements are made on a Perkin Elmer SYSTEM 7™ Thermal Analysis System. Melting information reported are second melting data, i.e., the sample is heated at a programmed rate of 10° C./min. to a temperature below its critical range. The sample is then reheated (2nd melting) at a programmed rate of 10° C./min.

A homogeneous ethylene/alpha-olefin copolymer can, in general, be prepared by the copolymerization of ethylene and any one or more alpha-olefin. For example, the alpha-olefin is a $C_3$-$C_{20}$ alpha-monoolefin, such as a $C_4$-$C_{12}$ or a $C_4$-$C_8$ alpha-monoolefin. For example, the alpha-olefin comprises at least one member selected from the group consisting of butene-1, hexene-1, and octene-1, i.e., 1-butene, 1-hexene, and 1-octene, respectively, or a blend of hexene-1 and butene-1.

Processes for preparing and using homogeneous polymers are disclosed in U.S. Pat. No. 5,206,075, to HODGSON, Jr., U.S. Pat. No. 5,241,031, to MEHTA, and PCT International Application WO 93/03093, each of which is hereby incorporated herein by reference thereto, in its entirety. Further details regarding the production and use of homogeneous ethylene/alpha-olefin copolymers are disclosed in PCT International Publication Number WO 90/03414, and PCT International Publication Number WO 93/03093, both of which designate Exxon Chemical Patents, Inc. as the Applicant, and both of which are hereby incorporated herein by reference thereto, in their respective entireties.

Still another species of homogeneous ethylene/alpha-olefin copolymers is disclosed in U.S. Pat. No. 5,272,236, to LAI, et al., and U.S. Pat. No. 5,278,272, to LAI, et al., both of which are hereby incorporated herein by reference thereto, in their respective entireties.

In one particular embodiment, the ethylene/alpha-olefin copolymer comprises a linear low density polyethylene (LLDPE) composed of copolymers of ethylene and comonomers of 1-butene. Desirably, the content of butene is from about 8 to 16 weight %. An exemplary commercially available LLDPE that can be used in accordance with the present invention is Sabic® 518N or Sabic 118N available from Saudi Basic Industries Corporation.

Adhesive layers 28a, 28b may include any suitable adhesive material, such as, e.g., anhydride-modified EVA copolymer, anhydride-modified EMA copolymer, and anhydride-modified EBA copolymer, unmodified EVA, unmodified EMA and unmodified EnBA with comonomer content of about 6 to 30 weight %.

Of the foregoing materials, anhydride-modified EVA copolymer is preferred, particularly those in which the vinyl acetate content thereof is 25 weight percent or more. A preferred such material is "BYNEL CXA E-361" from DuPont.

Adhesive layers 28a, 28b may comprise a material selected from the group consisting of anhydride-modified EVA copolymer; anhydride-modified ethylene/acrylate copolymer (e.g., anhydride-modified EMA copolymer, anhydride-modified ethylene/ethyl acrylate copolymer, and anhydride-modified EBA copolymer); anhydride-modified ethylene/alpha-olefin (EAO) copolymer (e.g., anhydride-modified linear low density polyethylene and anhydride-modified very low density polyethylene); homogeneous ethylene/alpha-olefin copolymer, particularly those having a density of less than about 0.89 g/cc (e.g., ethylene/octene copolymer); anhydride-modified high density polyethylene; and mixtures of the foregoing materials.

Suitable anhydride-modified EMA copolymers are commercially available from DuPont under the tradename BYNEL™, and from Quantum Chemicals under the tradename PLEXAR™ Anhydride-modified linear low density polyethylene is commercially available from Mitsui under the tradename ADMER™, and from DuPont under the tradename BYNEL™ Each of the other materials which can be used for adhesive layers 24 and 28 are also commercially available.

The total thickness of film 20 may range from about 25 to about 150 microns, with a range from about 50 to 100 microns being preferred. When present, interior layers 28a and 28b typically each comprise from about 20 to 40% of the thickness of the film, and in particular, from about 25 to 35% of the film's thickness, with about 30% of the film's thickness being somewhat more typical. Interior layers 28a, 28b of the film generally have a thickness from about 15 to 45 microns, and in particular, from about 30 to 30 microns. Exterior layers 22, 24 are typically of a thinner gauge than bulk interior layers 28a, 28b. For instance, exterior layers 22, 24 may each be about 25 to 75% of the thickness of interior layers 38a, 38b. In one embodiment, the exterior layers 22, 24 of the film may be from about 5 to 20 microns, with a thickness of 5 to 10 being preferred.

The interior layer 26 generally has a thickness that is from about 3 to 15 microns, with a thickness of about 5 to 10 being preferred. The adhesive layers 20a, 20b generally range from about 3 to 10 microns, and in particular from about 3 to 5 microns in thickness. It should be recognized that the overall thickness of the film and the thickness of individual layers is not limited to any specific range provided the desired properties and processability of the film is maintained.

As can be appreciated by those having ordinary skill in this art, the multilayer films of the present invention are not limited to the three or seven-layer structures described above. Films having fewer or greater numbers of layers, e.g., two, four, five, six, eight, nine, or more layers, are included within the scope of the present invention. For example, additional high density polyethylene layer(s) may be included in the film in order to increase the moisture barrier capabilities of the film if such an increase is desired. Additional oxygen barrier layer(s) may also be included if desired.

Various additives may used in any or all of the layers of the multilayer films of the present invention. Such additives include, without limitation, antiblocking agents, antioxidants, processing aids such as calcium stearate, pigments, antistatic agents, etc. Where the multilayer film is to be used to for making medical solution pouches, the amount of additive included in the film is preferably kept to a minimum in order to minimize the likelihood that such additives will be extracted into the medical solution.

The multilayer films of the present invention can be formed by cast coextrusion as a tubular film. Containers for medical applications or other end uses can be made directly from the coextruded, tubular film, or alternatively from rollstock material obtained from the tube after it has been slit and ply-separated. A hot blown process can also be used to make the film. Other processes, such as extrusion coating, conventional lamination, slot die extrusion, etc., can also be used to make the multilayer film of the present invention, although these alternative processes can be more difficult or less efficient than the above methods.

The multilayer films of the present invention have been described in connection with medical applications. However, it is to be understood that other applications for the films are also possible, and that this disclosure should not be construed as being limited only to medical pouches or devices.

The invention may be further understood by reference to the following examples, which are provided for the purpose of representation, and are not to be construed as limiting the scope of the invention.

EXAMPLES

The films produced in Examples were hot blown. The materials used in the films are identified below. All percentages are weight percents unless indicated otherwise. All physical property and compositional values are approximate unless indicated otherwise.

"SVSPI": Hybrar 5127; styrene-vinylisoprene-styrene block-co-polyisopyrene block copolymer available from Kuraray.

"EVA-1": Elvax 3165: 18.0 weight % vinyl acetate copolymer available from Dupont.

"PVDC": Ixan PV910; polyvinylidene chloride/methyl acrylate (8.5 weight % methyl acrylate) available from Solvin.

"LLDPE-1": Sabic 518N; linear low density polyethylene (1-butene based) available from Sabic.

"AB": Antiblock and wax.

"OBC": olefinic block copolymer available from Dow under the tradename Infuse D9100®.

In the following Examples 1-7, the noise dampening properties of a layer comprising EVA, an ethylene/alpha-olefin, and styrene-vinylisoprene-styrene block-co-polyisopyrene block copolymer were explored. The polymers were dry blended and then fed into a twin screw extruder to make a 2.0 mils thick cast monolayer film. Subsequently a film sample from each blend was tested per ASTM D4065 over a temperature range of 17° C. to 40° C. The results are summarized in Table 1 below.

TABLE 1

TAN DELTA DATA FOR POLYMER BLEND

| Experiment No. | Composition | Peak Tan Delta and Temperature, ° C. | Tan Delta at 23° C. | E" at 23° C., Dynes/sq · cm | E' at 23° C., Dynes/sq · cm |
|---|---|---|---|---|---|
| 1 | EVA-1[65%] + SVSPI[20%] + OBC[15%] | 0.339, 16.7 | 0.292 | 1.35E08 | 4.38E08 |
| 2 | EVA-1[50%] + SVSPI[20%] + OBC[30%] | 0.342, 16.7 | 0.317 | 1.40E08 | 4.61E08 |
| 3 | EVA-1[35%] + SVSPI[20%] + OBC[45%] | 0.350, 16.6 | 0.325 | 1.37E08 | 4.36E08 |
| 4 | EVA-1[20%] + SVSPI[20%] + OBC[60%] | 0.405, 18.1 | 0.381 | 1.26E08 | 3.40E08 |
| 5 | EVA-1[55%] + SVSPI[30%] + OBC[15%] | 0.409, 18.1 | 0.392 | 2.20E08 | 5.79E08 |
| 6 | EVA-1[40%] + SVSPI[30%] + OBC[30%] | 0.405, 18.1 | 0.390 | 1.89E08 | 5.01E08 |
| 7 | EVA-1[25%] + SVSPI[30%] + OBC[45%] | 0.471, 19.6 | 0.460 | 2.01E08 | 4.49E08 |

In the following Examples 8-11, the noise reduction and RF sealability of films in accordance with the invention were evaluated.

Control

A multilayer film in accordance with the present invention had the following 7-layer structure, with each layer being listed in the same order in which it appeared in the film:

| Layer No. | Function/Position | Layer Composition | Thickness (microns) | Vol. (%) |
|---|---|---|---|---|
| Layer 1 | First Exterior layer: | 95.0% EVA-1, 5% AB | 16.75 | 16.75 |
| Layer 2 | First Interior/Bulk Layer: | 95.0% EVA-1, 5% AB | 16.75 | 16.75 |
| Layer 3 | Adhesive/Tie Layer: | EVA-2 | 11.5 | 11.5 |
| Layer 4 | Barrier (Core) Layer: | PVDC | 10 | 10 |
| Layer 5 | Adhesive/Tie Layer: | EVA-2 | 11.5 | 11.5 |
| Layer 6 | Second Interior/Bulk Layer: | 95.0% EVA-1, 5% AB | 16.75 | 16.75 |
| Layer 7 | Second Exterior Layer: | 95.0% EVA-1, 5% AB | 16.75 | 16.75 |

Example 8

A multilayer film in accordance with the present invention had the following 7-layer structure, with each layer being listed in the same order in which it appeared in the film:

| Layer No. | Function/Position | Layer Composition | Thickness (microns) | Vol. (%) |
|---|---|---|---|---|
| Layer 1 | First Exterior layer: | 70.0% EVA-1, 25% LLDPE-1, 4.5% AB | 10.0 | 10.6 |
| Layer 2 | First Interior/Quiet Layer: | 50.0% EVA-1, 40% LLDPE-1, 10% SVSPI | 26.0 | 29.8 |
| Layer 3 | Adhesive/Tie Layer: | EVA-1 | 5.0 | 5.3 |
| Layer 4 | Barrier (Core) Layer: | PVDC | 8.0 | 8.6 |
| Layer 5 | Adhesive/Tie Layer: | EVA-1 | 5.0 | 5.3 |
| Layer 6 | Second Interior/Quiet Layer: | 50.0% EVA-1, 40% LLDPE-1, 10% SVSPI | 26.0 | 29.8 |
| Layer 7 | Second Exterior Layer: | 70.0% EVA-1, 25% LLDPE-1, 4.5% AB | 10.0 | 10.6 |

Example 9

A multilayer film in accordance with the present invention had the following 7-layer structure, with each layer being listed in the same order in which it appeared in the film:

| Layer No. | Function/Position | Layer Composition | Thickness (microns) | Vol. (%) |
|---|---|---|---|---|
| Layer 1 | First Exterior layer: | 70.0% EVA-1, 26% LLDPE-1, 4% AB | 10 | 10 |
| Layer 2 | First Interior/Quiet Layer: | 50.0% EVA-1, 36% LLDPE-1, 10% SVSPI, 4% AB | 30 | 30 |
| Layer 3 | Adhesive/Tie Layer: | EVA-1 | 5 | 5 |
| Layer 4 | Barrier (Core) Layer: | PVDC | 10 | 10 |
| Layer 5 | Adhesive/Tie Layer: | EVA-1 | 5 | 5 |
| Layer 6 | Second Interior/Quiet Layer: | 50.0% EVA-1, 36% LLDPE-1, 10% SVSPI 4% AB | 30 | 30 |
| Layer 7 | Second Exterior Layer: | 70.0% EVA-1, 26% LLDPE-1, 4% AB | 10 | 10 |

Example 10

A multilayer film in accordance with the present invention had the following 7-layer structure, with each layer being listed in the same order in which it appeared in the film:

| Layer No. | Function/Position | Layer Composition | Thickness (microns) | Vol. (%) |
|---|---|---|---|---|
| Layer 1 | First Exterior layer: | 70.0% EVA-1, 25% LLDPE-1, 4.5% AB | 7.0 | 10.0 |
| Layer 2 | First Interior/Quiet Layer: | 50.0% EVA-1, 40% LLDPE-1, 10% SVSPI | 21.5 | 30.7 |
| Layer 3 | Adhesive/Tie Layer: | EVA-1 | 4.0 | 5.7 |
| Layer 4 | Barrier (Core) Layer: | PVDC | 5.0 | 7.1 |
| Layer 5 | Adhesive/Tie Layer: | EVA-1 | 4.0 | 5.7 |
| Layer 6 | Second Interior/Quiet Layer: | 50.0% EVA-1, 40% LLDPE-1, 10% SVSPI | 21.5 | 30.7 |
| Layer 7 | Second Exterior Layer: | 70.0% EVA-1, 25% LLDPE-1, 4.5% AB | 7.0 | 10.0 |

Example 11

A multilayer film in accordance with the present invention had the following 7-layer structure, with each layer being listed in the same order in which it appeared in the film:

| Layer No. | Function/Position | Layer Composition | Thickness (microns) | Vol. (%) |
|---|---|---|---|---|
| Layer 1 | First Exterior layer: | 70.0% EVA-1, 25% LLDPE-1, 4.5% AB | 7.0 | 10.0 |
| Layer 2 | First Interior/Quiet Layer: | 40.0% EVA-1, 40% LLDPE-1, 20% SVSPI | 21.5 | 30.7 |
| Layer 3 | Adhesive/Tie Layer: | EVA-1 | 4.0 | 5.7 |
| Layer 4 | Barrier (Core) Layer: | PVDC | 5.0 | 7.1 |
| Layer 5 | Adhesive/Tie Layer: | EVA-1 | 4.0 | 5.7 |
| Layer 6 | Second Interior/Quiet Layer: | 40.0% EVA-1, 40% LLDPE-1, 20% SVSPI | 21.5 | 30.7 |
| Layer 7 | Second Exterior Layer: | 70.0% EVA-1, 25% LLDPE-1, 4.5% AB | 7.0 | 10.0 |

Observations and Results

Noise Reduction

The films of Examples 1-7 had a tan delta of 0.25 or greater over the temperature range of 17° C. to 40° C., which is indicative of the films ability to reduce noised and vibration. Accordingly, films employing such a layer would have good noise dampening properties.

The Control, which did not include any of the styrene-vinyl polyisoprene-styrene block-co-polyisopyrene block triblock polymer showed typical noise levels during crumpling and folding. In contrast, the films of Examples 8-11 which all included a quiet layer comprising a styrene-vinyl polyisoprene-styrene block-co-polyisopyrene block triblock polymer exhibited improved noise reduction over the temperature range of about 17° C. and 40° C. Accordingly, these films are particularly suited for use in ostomy applications.

RF Sealability

Films from the above Examples were also evaluated for RF sealability. The films were then sealed using radio frequency and seal peel strength was measured per ASTM F88. The films were sealed using a Strayfield Ltd RF sealing machine IPW9/SH with a supply frequency of 50 Hz, use frequency of 27.12 MHz. Two square samples were cut from each test film and these are sealed together to make a square pouch by applying the RF power source for 1.2 seconds, followed by cooling of 2.0 seconds. Several pouches were produced this way and then tested per ASTM F88. The control, which include 95% EVA and no EAO component in the outer two layers of the film exhibited good peel strength after RF sealing. The Control also had a dielectric loss factor of 0.09, which is indicative of RF sealability. Generally, a loss factor of 0.05 is indicative of a film's ability to be sealed with RF energy.

In particular, in Examples 8-11 the outer exterior layers and first and second interior layers (layers 2 and 6) comprised a combination of LLDPE and EVA. These films showed good RF sealability and all had a peel strength of greater than 500 g/inch.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A multilayer, sound dampening film comprising at least one quiet layer having noise dampening properties, the at least one quiet layer comprising a blend of an ethylene copolymer selected from the group consisting of ethylene vinyl acetate, ethylene methyl acrylate, ethylene butyl acrylate, ethylene-co-n-butyl acrylate-co-carbon monoxide, ethylene-co-n-vinyl acetate-co-carbon monoxide, ethylene-co-n-butyl acrylate-co-glycidyl methacrylate, and combinations thereof and from 5 to 50 weight percent of a styrene-vinyl polyisoprene-styrene triblock polymer, wherein the quiet layer has a Tangent Delta value of at least 0.27 at a temperature range between 17° C. and 40° C., and wherein the film has only a single barrier layer, and wherein said single barrier layer comprises polyvinylidene chloride (PVDC).

2. The film of claim 1, wherein the quiet layer further comprises an ethylene/alpha olefin.

3. The film of claim 2, wherein the ethylene/alpha olefin is linear low density polyethylene having a density from 0.84 to 0.91 g/cm$^3$.

4. The film of claim 1, wherein the quiet layer is disposed between two exterior layers.

5. The film of claim 4, wherein the quiet layer comprises from about 20 to 65 weight percent of said ethylene copolymer, from 15 to 60 weight percent of an ethylene/alpha olefin, and from 10 to 50 weight percent of said styrene-vinyl polyisoprene-styrene triblock polymer.

6. The film of claim 5, wherein the copolymer is selected from the group consisting ethylene methyl acrylate, ethylene vinyl acetate and ethylene butyl acrylate, and combinations thereof.

7. The film of claim 4, wherein the quiet layer comprises a combination of said ethylene copolymer, an ethylene/alpha olefin, and said styrene-vinyl polyisoprene-styrene triblock polymer, and wherein the exterior layers of the film comprise a blend of a copolymer selected from the group consisting of ethylene vinyl acetate, ethylene methyl acrylate, ethylene butyl acrylate, and combinations thereof, and an ethylene/alpha olefin, wherein the copolymer is present in the exterior layer in an amount that is at least 50 percent by weight.

8. The film of claim 7, wherein the copolymer is ethylene vinyl acetate (EVA).

9. The film of claim 1, wherein, the film includes two of said at least one quiet layers, and wherein said two quiet layers are interior layers of the film.

10. A noise dampening film comprising two exterior layers, two interior quiet layers disposed between a barrier layer and the exterior layers, the quiet layers comprising from 5 to 50 weight percent of a styrene-vinyl polyisoprene-styrene polymer and an ethylene copolymer selected from the group consisting of ethylene vinyl acetate, ethylene methyl acrylate, ethylene butyl acrylate, ethylene-co-n-butyl acrylate-co-carbon monoxide, ethylene-co-n-vinyl acetate-co-carbon monoxide, ethylene-co-n-butyl acrylate-co-glycidyl methacrylate, and combinations thereof, and wherein the quiet layers each have a Tangent Delta value of at least 0.27 at a temperature range between 17° C. and 40° C., wherein the film has only a single barrier layer, and wherein said single barrier layer comprises polyvinylidene chloride.

11. The film of claim 10, wherein the quiet layers include up to 80 weight percent of said ethylene copolymer.

12. The film of claim 10, wherein the film is RF sealable to itself and the two exterior layers each comprise a blend of an ethylene/alpha olefin and 20% to 80% by weight of an ethylene copolymer, and the quiet layers include up to 80 weight percent of said ethylene copolymer.

13. A pouch for the packaging and administration of medical solutions, the pouch being formed from the film of claim 10.

14. A pouch for the collection of human drainage, the pouch being formed from the film of claim 10.

15. A multilayer film consisting of 7 layers, the film comprising:
   first and second exterior layers each comprising a blend of an ethylene/alpha olefin and 20% to 80% by weight of a copolymer selected from the group consisting of an ethylene acrylate copolymer, ethylene vinyl acetate, and combinations thereof;
   a barrier layer of polyvinylidene chloride (PVDC) disposed between the first and second exterior layers;
   first and second quiet interior layers disposed on opposite sides of the barrier layer, each quiet layer comprising a blend of an ethylene/alpha olefin, 20% to 80% by weight of a copolymer selected from the group consisting of an ethylene acrylate copolymer, ethylene vinyl acetate, and combinations thereof, and from 10 to 50 weight percent of a styrene-vinyl polyisoprene-styrene triblock polymer, wherein the quiet layers each have a Tangent Delta value of at least 0.27 at a temperature range between 17° C. and 40° C., and
   a pair of adhesive layers that are each disposed between one of the first and second interior layers and the barrier layer.

16. The film of claim 15, wherein the first and second exterior layers comprise a blend of a linear low density polyethylene and at least 50% by weight of an ethylene vinyl acetate copolymer.

17. The film of claim 15, wherein the first and second exterior layers each comprise 50 to 70 weight percent ethylene vinyl acetate copolymer, and the first and second interior layers each comprise 40 to 60 weight percent ethylene vinyl acetate copolymer.

18. The film of claim 17, wherein the ethylene/alpha olefin is linear low density polyethylene.

19. The film of claim 15, wherein the ethylene acrylate copolymer is selected from the group consisting ethylene methyl acrylate and ethylene butyl acrylate, and combinations thereof.

20. The film of claim 15, wherein the adhesive layers comprise an ethylene acrylate copolymer, ethylene vinyl acetate, or a combination thereof.

* * * * *